United States Patent [19]

Yun et al.

[11] Patent Number: 5,627,305

[45] Date of Patent: May 6, 1997

[54] GAS SENSING APPARATUS AND METHOD

[75] Inventors: Dong H. Yun, Anyang-si; Chul H. Kwon; Kyuchung Lee, both of Seoul; Hyung K. Hong, Kwacheon-si; Hyeon S. Park, Seoul; Hyun W. Shin, Kwacheon-si; Sung T. Kim, Seoul, all of Rep. of Korea

[73] Assignee: LG Electronics Inc., Seoul, Rep. of Korea

[21] Appl. No.: 605,889

[22] Filed: Feb. 23, 1996

[30] Foreign Application Priority Data

Feb. 24, 1995 [KR] Rep. of Korea .............. 3681/1995

[51] Int. Cl.$^6$ .......................... G01N 27/04; G01N 31/12; G01R 3/00
[52] U.S. Cl. .......................... 73/23.2; 73/31.06; 73/29.01; 73/23.34; 340/632; 422/83; 422/94; 422/98; 338/34
[58] Field of Search .................. 73/23.2, 31.06, 73/29.01, 30.01, 23.3, 23.31, 23.32, 23.34; 340/632, 634; 338/34; 422/83, 90, 94, 98

[56] References Cited

U.S. PATENT DOCUMENTS

| | | |
|---|---|---|
| 4,553,424 | 11/1985 | Sakurai et al. .................. 73/27 R |
| 4,587,104 | 5/1986 | Yannopoulos ..................... 422/94 |
| 4,706,493 | 11/1987 | Chang et al. ..................... 73/23 |
| 4,720,993 | 1/1988 | Badwal ............................. 73/23 |
| 4,770,027 | 9/1988 | Ehara et al. ....................... 73/23 |
| 4,884,435 | 12/1989 | Ehara ................................ 73/23 |
| 4,911,892 | 3/1990 | Grace et al. ..................... 422/94 |
| 4,977,658 | 12/1990 | Awano et al. ................. 29/25.01 |
| 5,045,285 | 9/1991 | Kolesar, Jr. ..................... 422/98 |
| 5,047,214 | 9/1991 | Fukui et al. ..................... 422/98 |
| 5,402,665 | 4/1995 | Hart et al. ......................... 73/16 |

*Primary Examiner*—Hezron E. Williams
*Assistant Examiner*—J. David Wiggins
*Attorney, Agent, or Firm*—Morgan, Lewis and Bockius LLP

[57] ABSTRACT

A gas sensing apparatus is disclosed including a gas sensing device that is self-heated due to an applied voltage, whose resistance variation amount is varied to thereby sense gas; a voltage supply for variably supplying a voltage to the gas sensing device; a current detector for detecting the current flowing through the gas sensing device thereby generating a current-voltage characteristic for the gas sensing apparatus under the effect of a given gas exposure; and a control and judgement portion for controlling the voltage supply to control a variation value of a voltage supplied to the gas sensing device and to determine the kind and density of a gas in an ambient atmosphere, using current-voltage characteristic reference data.

7 Claims, 5 Drawing Sheets

GAS SENSING APPARATUS AND METHOD

BACKGROUND OF THE INVENTION

1. Field of the Invention

The present invention relates to a gas sensing apparatus and, mole particularly, to a low-power, normal-temperature type gas sensing apparatus and method whose sensing operation is made using current-voltage characteristics of a sensing layer without a separate heater.

2. Discussion of the Related Art

Generally, a gas sensing apparatus is constructed in such a manner that a heater is formed in a gas sensing device which directly senses gas. Therefore, when a voltage is applied to the heater, heat is generated to heat a sensing layer of the sensing device to a high temperature (200°–500° C.). The reason to heat the sensing layer using the heater formed in the gas sensing device will be explained below.

The sensing layer of the gas sensing device is formed of a semiconductor oxide as a main material with a metal catalyst like Pt, Au, or Ag added. The sensing operation is performed so that the sensing layer measures the change of the semiconductor oxide's electric conductivity in the presence of gas. The aforementioned semiconductor' oxide has a relatively high resistance (over several $M\Omega$s) at room temperature. However, in case that the temperature is increased to a relatively high temperature above 200° C., the semiconductor oxide has tens or hundreds of $K\Omega$ in resistance and will react with various types of reducing gas that may be present in the ambient atmosphere.

As described above, a heater has been required in order to make the sensing layer react with the gas and thereby to exhibit a variation in the rate of electric conductivity.

The aforementioned conventional gas sensing device and sensing apparatus will be explained below with reference to the accompanying drawings. FIG. 1 is a cross-sectional view of the conventional gas sensing device. FIG. 2 is a plan view of the conventional gas sensing device.

The conventional gas sensing device is constructed in a manner that a heater 3 for heating a sensing layer and two electrodes 2 for measuring the variation of electric conductivity of the sensing layer are formed on an alumina ($Al_2O_3$) substrate 1 by a screen printing method. The sensing layer 4 for sensing gas is formed over the two electrodes 2. At this time, the sensing layer 4 is formed of a semiconductor oxide in which $SnO_2$ and metal catalyst like Pt, Au, or Ag are mixed. The heater 3 is placed on the back surface of the alumina substrate 1 as shown in FIG. 1, or on the front surface of the substrate 1 on which the electrodes are formed, as shown in FIG. 2.

The conventional gas sensing apparatus which senses gas using the aforementioned gas sensing device will be explained below. FIG. 3 is a block diagram of the conventional gas sensing apparatus.

The conventional gas sensing apparatus is constructed with a gas sensing device 11 shown in FIGS. 1 and 2, a heater driver 12 (heater voltage supply) for driving the heater 3 of the gas sensing device 11, a voltage supply 13 for supplying a voltage to the electrodes of the gas sensing device 11, a current detector 14 for detecting a current that varies in accordance with gas detected by the gas sensing device ill, and a control and judgement portion 15 that controls the voltage supply 13 and heater driver 12, and receives a current detected from the current detector 14 to judge whether or not a gas is present.

The voltage supply 13 and heater driver 12 are controlled by the control and judgement portion 15 so that the voltage supply 13 supplies a voltage to the electrodes 2 of the gas sensing device 11 and the heater driver 12 supplies power to the heater 3 of the gas sensing device 11 to heat the sensing layer 4 to a high temperature i.e., above 200° C. In this state, when the gas sensing device is exposed to gas, the resistance of the sensing layer 4 varies If the sensing layer 4 is exposed to gas and reacts therewith, the resistance value of the sensing layer 4 is changed into a resistance value lower than that of the sensing layer in air. Therefore, if a uniform voltage is supplied from the voltage supply 13 to the gas sensing device 11, the current is output at a high level. Accordingly, the current detector 14 detects the current which runs through the sensing layer, and applies it to the control and judgement portion 15.

A gas sensing operation is performed so that the control and judgement portion 15 compares the current input from the current detector 14 to measure the electric conductivity of the sensing layer of the gas sensing device 11. That is, in the conventional gas sensing apparatus, a uniform voltage is supplied from the voltage supply 13, and gas detection is accomplished in accordance with the current value detected by the current detector 14.

However, the conventional gas sensing apparatus has several problems. First, the heater and heater driver for heating the sensing layer to a proper temperature are required separately. This complicates the gas sensing apparatus, decreases its productivity, and increases the cost.

Secondly, power consumption is increased because the device is heated to a high temperature. In addition, due to thermal shock, the gas sensing device will deteriorate and may even break causing the reliability of the gas sensing device to be low.

Thirdly, the conventional gas sensing apparatus is capable of sensing the density of gas, but incapable of judging the kind of gas.

OBJECTS AND SUMMARY OF THE INVENTION

An object of the present invention is a gas sensing, apparatus and method in which gas is sensed at normal temperature and without the use of a separate heater.

Another object of the present invention is a gas sensing apparatus and method that uses current-voltage characteristics of a sensing layer which reacts with gas without a separate heater.

To accomplish these and other objects of the present invention, there is provided a gas sensing apparatus including a gas sensing device having a resistance variation amount that is varied to sense gas; a voltage supply for variably supplying a voltage to the gas sensing device; a current detector for detecting a current varying with the gas sensed by the gas sensing device; and a control and judgment portion for controlling the voltage supply to control a variation value of a voltage supplied to the gas sensing device, the control and judgement portion receiving a current value from the current detector to judge the kind and density of gas, using current-voltage characteristic reference data.

There is further provided a gas sensing method for sensing gas using a gas sensing device having a sensing layer self-heated by a supplied voltage to react with gas, the method including the steps of storing current-voltage characteristic data in accordance with the kind and density of gas; linearly varying a voltage and supplying it to the gas sensing device, and detecting variations in current value; and obtaining current-voltage characteristics from the variable voltage supply and a current value detected therefrom, and comparing the current-voltage characteristics with the previously stored data, to sense the gas.

BRIEF DESCRIPTION OF THE ATTACHED DRAWINGS

DETAILED DESCRIPTION OF THE INVENTION

A preferred embodiment of the present invention will be explained below with reference to the accompanying drawings. In the gas sensing device of the present invention, in order to measure the variation of electric conductivity of the sensing layer without heating a semiconductor oxide of a sensing material using an external heater, the sensing layer is self-heated due to an applied voltage so that the self-heated portion of the sensing layer sensitively reacts in response to the presence of a gas in an ambient atmosphere to be detected.

Figure 1:
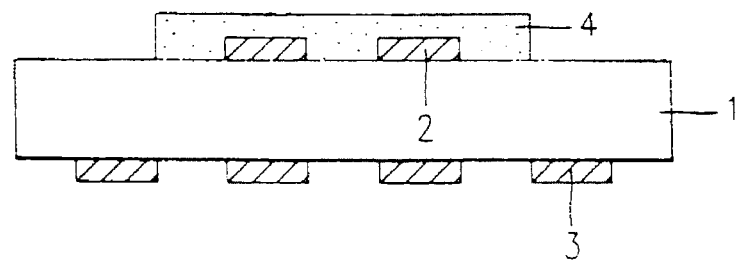
FIG. 1 is a cross-sectional view of a conventional gas sensing device.
Figure 2:
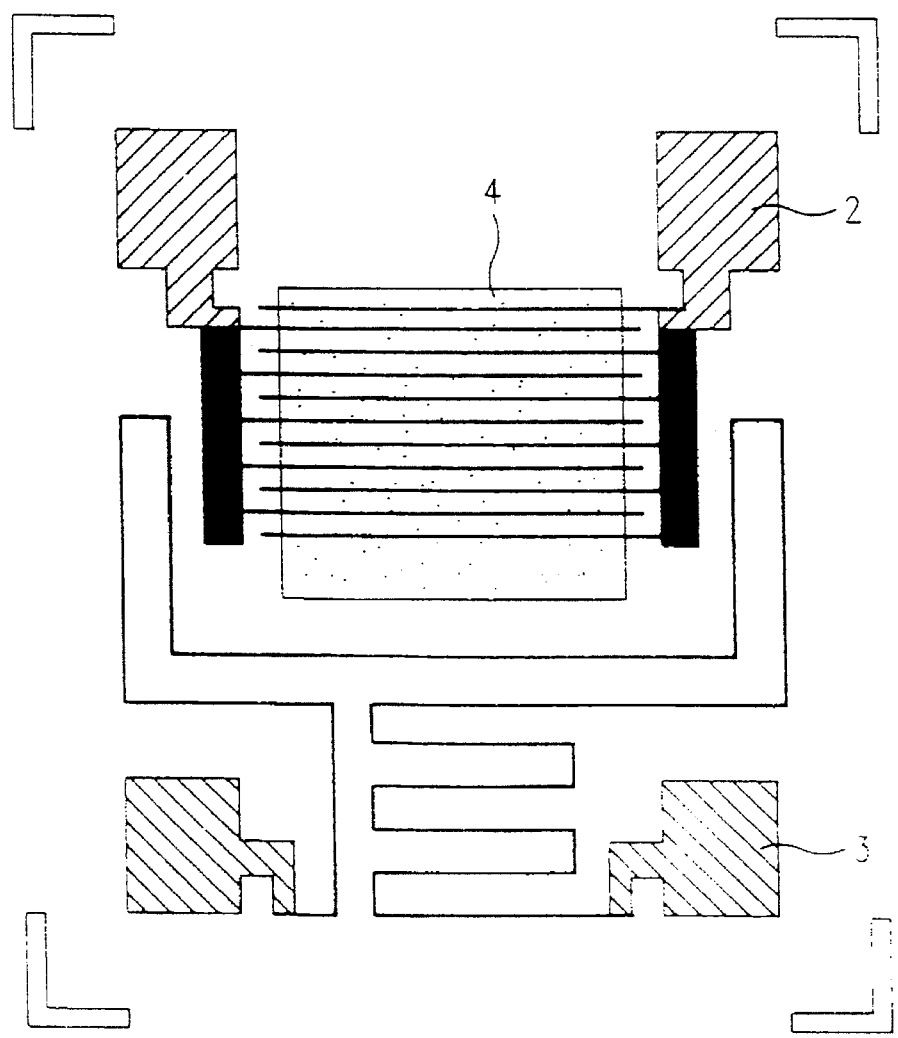
FIG. 2 is a plan view of a conventional gas sensing device.
Figure 3:
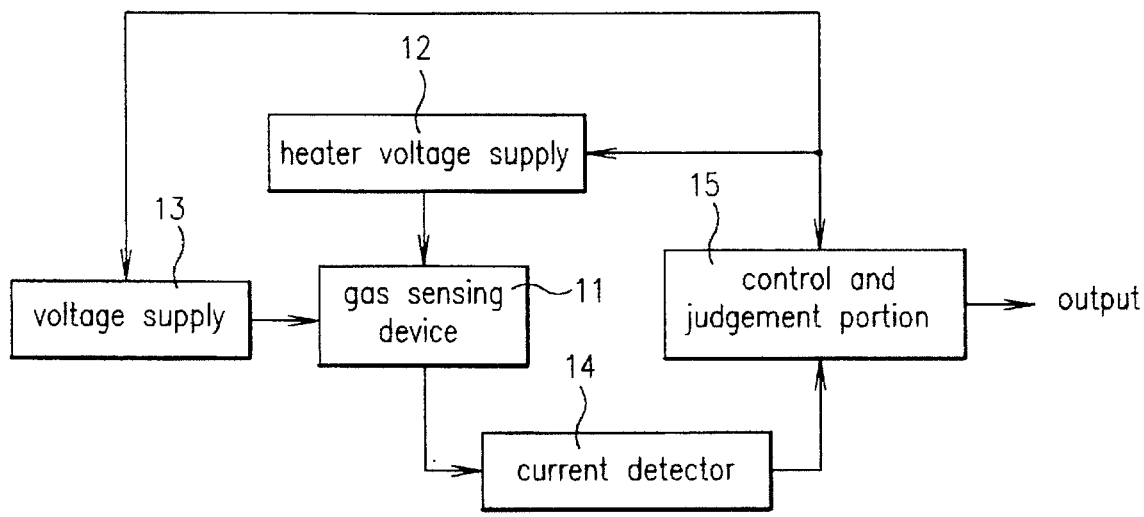
FIG. 3 is a block diagram of a conventional gas sensing device.
Figure 4:
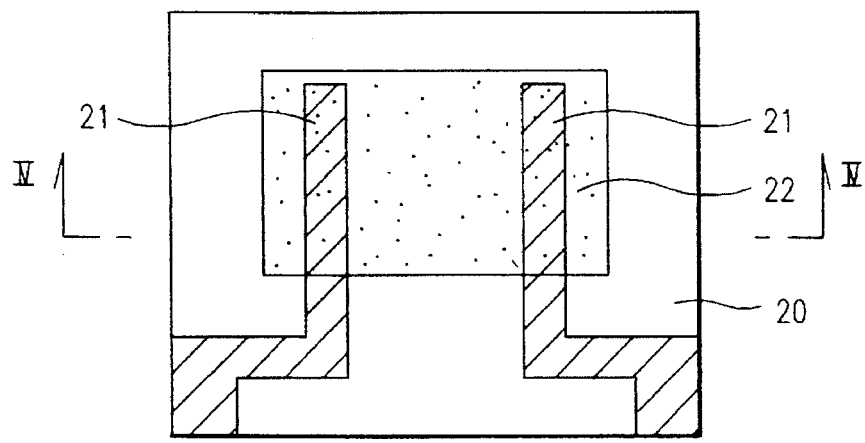
FIG. 4 is a layout of a gas sensing device in accordance with the present invention.
Figure 5:
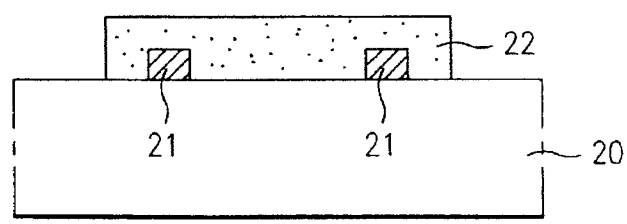
FIG. 5 is a cross-sectional view taken along line IV—IV shown in FIG. 4.

The gas sensing device according to the present invention is illustrated in FIGS. 4–5, as composed of two electrodes 21 formed on a predetermined portion of an alumina substrate 20, and a sensing layer formed over the two electrodes 21 to react with external gas.

A, method of fabricating the gas sensing device of the present invention constructed as above will be explained below. First, two electrodes 21 are formed on the alumina substrate 20 using Pt paste through a screen printing method so that the surface of the sensing layer is activated for the complete oxidation of the gas to be sensed, resulting in improvement of sensitivity.

The two patterned electrodes 21 are sintered at a temperature of about 1100° C. for one hour. Then, a sensing layer paste formed both of $SnO_2$ and $WO_3$ powder mixed at a rate of 95:5 wt % and of an organic compound is screen-printed on the electrodes 21 to form the sensing layer 22. The organic compound could include, for example, Al, Ni, Cu, Sn or Fe (this list is merely illustrative and directed to known elements utilized in the art and is not intended to limit the disclosure to the cited elements) as the metallic organic compound. After the sensing layer 22 is sintered at a temperature of about 600° C. for one hour, a lead wire is connected to the pad of electrodes 21 and the device is packaged.

Figure 6:
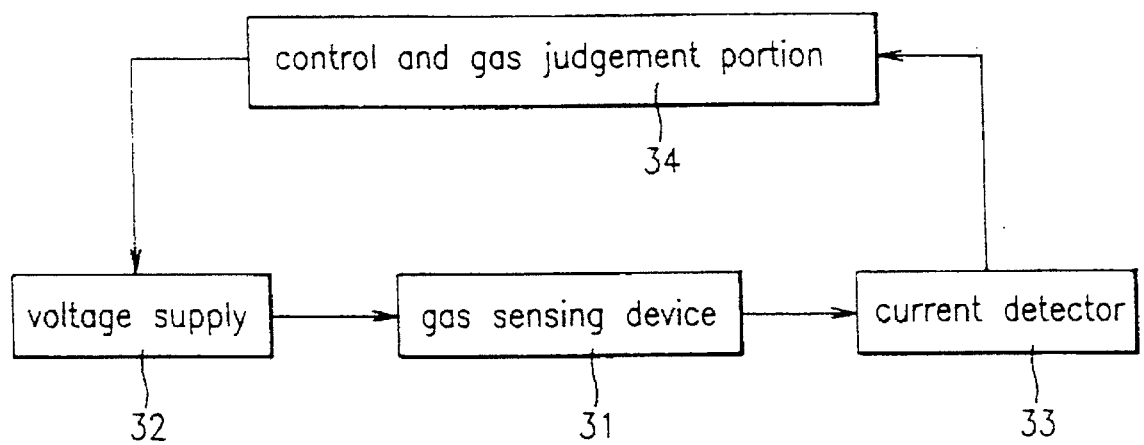
FIG. 6 is a block diagram of a gas sensing apparatus in accordance with the present invention.

A gas sensing apparatus using the aforementioned gas sensing device in accordance with the present invention will be described below. FIG. 6 is a block diagram of the gas sensing apparatus according to the present invention.

The gas sensing apparatus in accordance with the present invention is constructed of a gas sensing device without a heater as shown in FIG. 6, a voltage supply 32 for variably supplying a voltage to the gas sensing device, a current detector 33 for detecting a current that varies in accordance with the gas sensed by the gas sensing device, and a control and judgment portion for controlling the voltage supply to control the value of a voltage supplied to the gas sensing device. The portion 34 also receives a current value from the current detector to judge the kind and density of gas using prestored current-voltage characteristics.

Figure 7A:
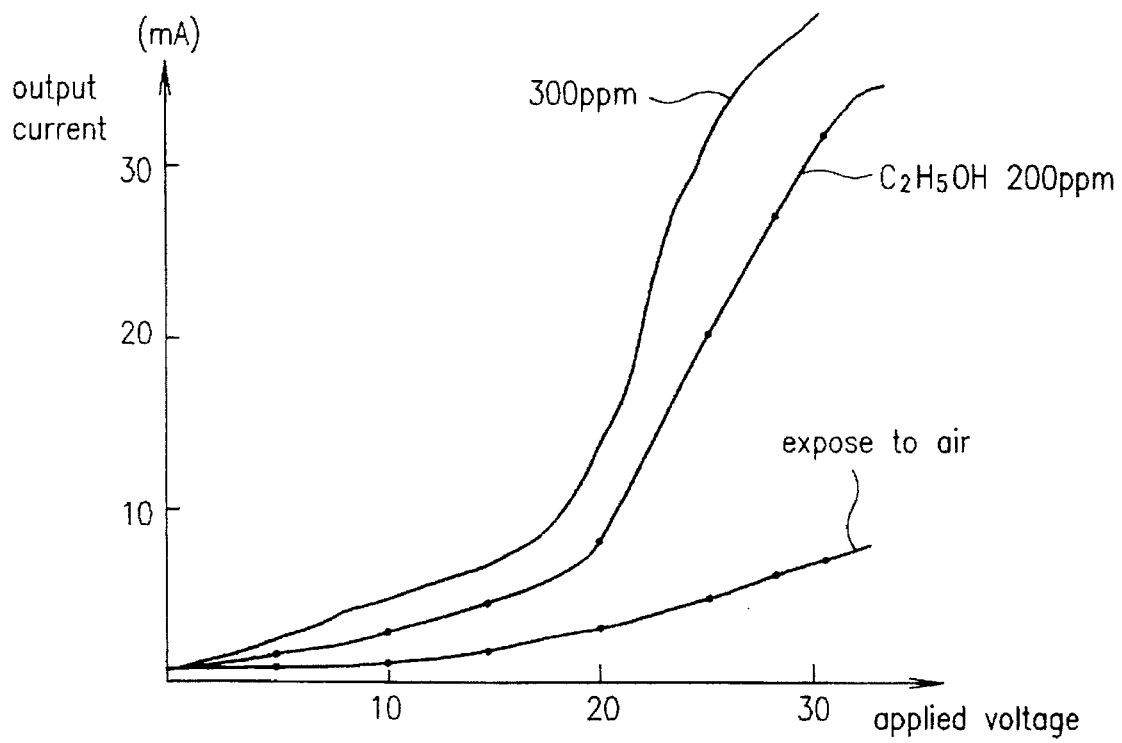
FIGS. 7A, 7B and 7C show operation characteristics of a gas sensing apparatus in accordance with the present invention.
Figure 7B:
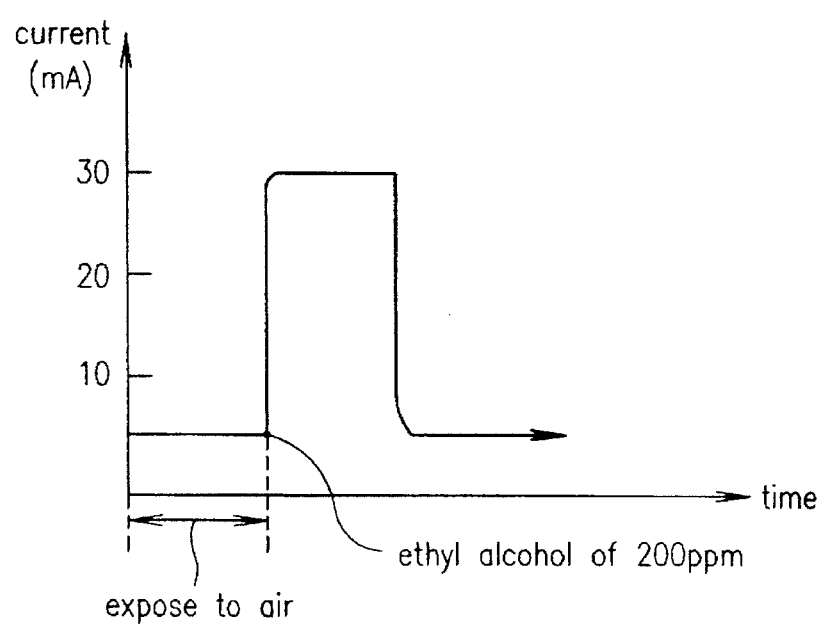
Figure 7C:
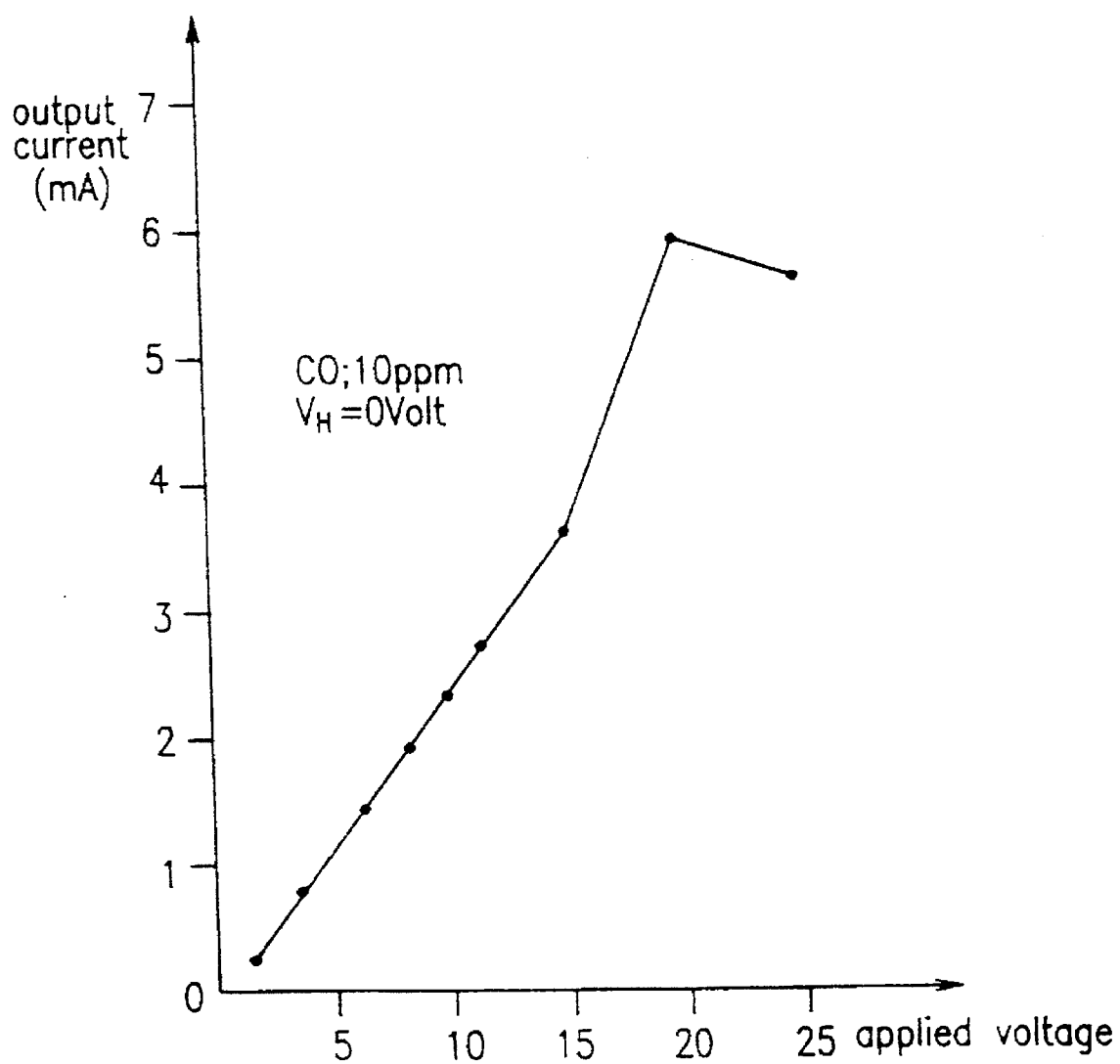

The operation of the gas sensing apparatus of the present invention will be explained below. FIGS. 7A to 7C show operation characteristics of the gas sensing apparatus in accordance with the present invention. FIG. 7A shows a current value, which is detected when the gas sensing device is exposed in the air and in a gas $C_2H_5OH$ gas having a density of 200 PPM and $C_2H_5OH$ gas having a density of 300 PPM) while the voltage supplied to the gas sensing device varies. FIG. 7B shows the relationship between time and current value detected when the gas sensing device is exposed to ethylalcohol (200 PPM) and electrically energized to a state of 30 V. FIG. 7C shows current-voltage characteristics with respect to CO gas.

A method of sensing gas using the gas sensing device without a heater will be explained. The control and judgment portion 34 controls the voltage supply 32 in order to vary the voltage supplied to the gas sensing device to judge the current detected over time.

As described above, the voltage supplied to the gas sensing device varies and the current at this time is detected, in order to judge the kind and density of gas in accordance with current variation amount/voltage variation amount. That is, as the applied voltage becomes higher, heat generation of the sensing layer 22 becomes larger. This reduces the resistance of the sending layer 22, increasing the detected current, proportional to the supplying voltage.

However, the amount of voltage variation and current variation are nearly uniform in air. On the contrary, the characteristics in the ambient of ethylalcohol ($C_2H_5OH$) is opposite to the characteristics in air. Specifically, the current-voltage characteristics at a low voltage (0–15 V) is similar to that in the air, but an abrupt current increase occurs at a voltage above 20 V.

At a relatively low voltage, reactivity between the sensing layer and alcohol is low due to less self-hearing of the sensing layer. At a higher voltage, reactivity between the sensing layer and alcohol is high due to greater self-heating of the sensing layer. Even the same kind of gas may exhibit current increase corresponding to its density. That is, in the case that the sensing layer reacts with the ethylalcohol of 200 PPM, the current increase is different from the case of 300 PPM. Gas can be sensed using the current voltage characteristics as described above.

FIG. 7B shows the current-voltage characteristic in the case that the supplied voltage is fixed at 30 V and the gas sensing device is exposed to air or a gas. A current of about 5 mA flows in the air, the current is abruptly increased to 30 mA in case that the sensing device is exposed to ethylalcohol of 200 PPM. In case that ethylalcohol is removed, the current of the sensing device will recover to its normal non-exposed state.

As described above, the current-voltage characteristics of the gas sensing device are always the same regardless of the thickness of the sensing layer 22 of the gas sensing device 31 and the interval/distance between the electrodes (only the applied voltage and the absolute value of the current are changed).

The current-voltage characteristics on the reducing gas of the gas sensing device of the present invention is shown in FIG. 7C. Here, CO is taken as an illustrative example for the reducing gas. In this case, and different from the effects of ethylalcohol, an abrupt current increase occurs around 15 V, but the current is reduced by a narrow range at a high voltage about 20 V. This is because, at a low voltage, heat increases due to the increase of the voltage and thus the temperature and reactivity with CO increase to increase the current abruptly. However, at a voltage above 20 V, the heat will reduce the reaction rate with CO.

The aforementioned characteristics are consistent with general principle in which the reactivity between CO gas and the sensing layer increases proportionally to temperature at a low temperature (below 300° C.), but the reactivity rate reduces at a high temperature.

The simulation result data as described above is previously stored in the control and judgment portion 34, and then the variation amount of the voltage supplied to the gas sensing device and the variation amount of the current detected from the gas sensing device at this time are recognized and compared with the previously scored simulation data, in order to judge the kind and density of gas.

The aforementioned gas sensing apparatus and the method of fabricating the gas sensing device in accordance with the present invention has the following effects.

First, the gas sensing device of the present invention has the sensing layer self-heated using the voltage supplied to the sensing layer, resulting in no requirement of a heater and heater driver. This simplifies the system design and realizes a low-power sensing device. Also, this improves productivity and reduces production cost.

Secondly, elimination of the heater reduces thermal shock and improves the reliability of the device.

Thirdly, various kinds of gas can be sensed using the current-voltage characteristic of the sensing layer which vary with the kind and density of gas.

We claim:

1. A gas sensing apparatus comprising:
    a semiconductor oxide type gas sensing device including a sensing layer, the sensing layer having an electrical resistance that varies upon reaction with an ambient gas;
    a voltage supply for supplying a variable voltage to the gas sensing device;
    a current detector for detecting a current level flowing through the sensing layer during a variation of the voltage supplied to the gas sensing device; and
    a control and judgement circuit for controlling the voltage supply to apply the variable voltage to the gas sensing device and for receiving the detected current level from the current detector to identify the kind and density of the ambient gas by correlating the voltage applied to the gas sensing device with the detected current level with previously stored voltage/current reference data.

2. A gas sensing apparatus according to claim 1, wherein the gas sensing device comprises:
    a substrate having said sensing layer formed thereon, said sensing layer having a first side and a second side; and
    electrodes coupled to said first side and second side of said sensing layer for supplying a voltage to said sensing layer and for outputting a current corresponding to the current flowing through said sensing layer in response to said applied voltage.

3. A gas sensing apparatus according to claim 1, wherein the sensing layer includes a chemical mixture comprising $SnO_2$, $WO_3$ powder, and an organic compound overlaying the electrodes.

4. A gas sensing apparatus according to claim 3, wherein said electrodes are formed of Pt paste applied to said substrate.

5. A gas sensing apparatus according to claim 3, wherein the mixture ratio of said $SnO_2$ and $WO_3$ powder of said sensing layer is 95:5 wt %.

6. A gas sensing apparatus according to claim 2, wherein the application of a supplied voltage to the electrodes results in a self-heating of the sensing layer.

7. A gas sensing method for sensing gases using a gas sensing device having a sensing layer that has a voltage supplied thereto in which the sensing layer is self-heated by the supplied voltage and that reacts with particular gases of interest and a current detection circuit for detecting the current level flowing through the sensing layer, the method comprising the steps of:
    storing current-voltage reference data corresponding to measured values of current flowing through the sensing layer for a plurality of voltages for each of a plurality of gases at different densities for the plurality of gases in an ambient atmosphere;
    applying a variable voltage to the self-heated sensing layer and detecting the resultant currents flowing through the sensing layer;
    referencing the stored current-voltage reference data in accordance with the measured voltage supplied to the sensing layer and the corresponding detected current level flowing through the sensing layer for the supplied voltage; and
    identifying the kind and density of the particular gases of interest by identifying the kind and density of gas corresponding to the current/voltage reference data that most closely matches the applied voltage and resultant current levels.

* * * * *